US011927532B2

(12) United States Patent
Miyashita et al.

(10) Patent No.: US 11,927,532 B2
(45) Date of Patent: Mar. 12, 2024

(54) COMPONENT ANALYSIS DEVICE AND COMPONENT ANALYSIS METHOD

(71) Applicant: Panasonic Intellectual Property Management Co., Ltd., Osaka (JP)

(72) Inventors: Mariko Miyashita, Hyogo (JP); Tatsushi Ohyama, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 617 days.

(21) Appl. No.: 17/124,645

(22) Filed: Dec. 17, 2020

(65) Prior Publication Data

US 2021/0102896 A1    Apr. 8, 2021

Related U.S. Application Data

(63) Continuation of application No. PCT/JP2019/030195, filed on Aug. 1, 2019.

(30) Foreign Application Priority Data

Aug. 28, 2018 (JP) .................. 2018-159450
Jul. 19, 2019 (JP) .................. 2019-133476

(51) Int. Cl.
*G01N 21/64* (2006.01)
*G01N 33/02* (2006.01)

(52) U.S. Cl.
CPC ..... *G01N 21/6428* (2013.01); *G01N 21/6408* (2013.01); *G01N 33/02* (2013.01); *G01N 2201/129* (2013.01)

(58) Field of Classification Search
None
See application file for complete search history.

(56) References Cited

U.S. PATENT DOCUMENTS

2007/0037135 A1* 2/2007 Barnes ............... G01N 21/51
                                                    356/73
2009/0024360 A1* 1/2009 Arnvidarson ......... G01J 3/45
                                                    356/451
(Continued)

FOREIGN PATENT DOCUMENTS

CN    105699345    6/2016
CN    107561046    1/2018
(Continued)

OTHER PUBLICATIONS

Yu et al. (Impact of dataset diversity on accuracy and sensitivity of parallel factor analysis model of dissolved organic matter fluorescence excitation-emission matrix, Scientific Reports, Received: Oct. 12, 2014, Accepted; Apr. 7, 2015, Published: May 11, 2015; www.nature.com/scientificreports).*

(Continued)

*Primary Examiner* — Hugh Maupin
(74) *Attorney, Agent, or Firm* — Rimon, P.C.

(57) ABSTRACT

A component analysis device includes a data acquisition circuit that acquires spectral data of an analyte containing components, the spectral data being obtained by measuring a spectrum of the analyte with a sensor, a type acquisition circuit that acquires information indicating a type of the analyte, a storage that stores a reference spectral data set including multiple spectral data of substances each of which is estimated to be included in the analyte, the reference spectral data set corresponding to the type of the analyte, and an analysis circuit that performs a parallel factor analysis by using, as input data, the spectral data of the analyte and the reference spectral data set.

6 Claims, 12 Drawing Sheets

(56) References Cited

U.S. PATENT DOCUMENTS

| | | | | |
|---|---|---|---|---|
| 2009/0306932 | A1* | 12/2009 | Li | G01N 21/64 |
| | | | | 702/179 |
| 2011/0125477 | A1* | 5/2011 | Lightner | G05B 13/048 |
| | | | | 703/11 |
| 2012/0228519 | A1* | 9/2012 | Gilmore | G01N 33/18 |
| | | | | 356/432 |
| 2012/0280146 | A1 | 11/2012 | Rizkallah et al. | |
| 2013/0112895 | A1 | 5/2013 | Birlouez-Aragon et al. | |
| 2014/0362375 | A1 | 12/2014 | Ikeda | |
| 2015/0044098 | A1* | 2/2015 | Smart | A61B 5/0084 |
| | | | | 422/82.05 |
| 2016/0123882 | A1* | 5/2016 | Gilmore | G01N 21/85 |
| | | | | 250/227.11 |
| 2018/0150616 | A1 | 5/2018 | Akamaru | |
| 2018/0375743 | A1* | 12/2018 | Lee | G06F 17/16 |
| 2019/0204577 | A1* | 7/2019 | Faris | H04N 23/67 |
| 2019/0369013 | A1* | 12/2019 | Birlouez-Aragon | G01N 21/35 |
| 2020/0103328 | A1* | 4/2020 | Ozcan | G01N 15/1434 |

FOREIGN PATENT DOCUMENTS

| | | |
|---|---|---|
| JP | 2004-184132 | 7/2004 |
| JP | 2009-139299 | 6/2009 |
| JP | 2011-203097 | 10/2011 |
| JP | 2011-257218 | 12/2011 |
| JP | 2013-514530 | 4/2013 |
| JP | 2013-528814 | 7/2013 |
| JP | 2015-130864 | 7/2015 |
| JP | 2015-180895 | 10/2015 |
| JP | 2016-099282 | 5/2016 |
| JP | 2018-087700 | 6/2018 |
| WO | 2010/132823 | 11/2010 |
| WO | 2013/099928 | 7/2013 |

OTHER PUBLICATIONS

International Search Report of PCT application No. PCT/JP2019/030195 dated Oct. 21, 2019.

Jakob Christensen et al., "Multivariate Autofluorescence of Intact Food Systems", Chemical Reviews, vol. 106, No. 6, May 5, 2006, pp. 1979-1994.

L. Rubio et al., "Standard addition method based on four-way PARAFAC decomposition to solve the matrix interferences in the determination of carbamate pesticides in lettuce using excitation-emission fluorescence data", Talanta, vol. 138, Jun. 1, 2015, pp. 86-99, <http://dx.doi.org/10.1016/j.talanta.2015.01.042>.

Erdal Dinc et al., "Multiway analysis methods applied to the fluorescence excitation-emission dataset for the simultaneous quantification of valsartan and amlodipine in tablets", Spectrochimica Acta Part A: Molecular and Biomolecular Spectroscopy, vol. 184, Sep. 5, 2017, pp. 255-261, <http://dx.doi.org/10.1016/j.saa.2017.04.081>.

C. W. Cuss et al., "Combining parallel factor analysis and machine learning for the classification of dissolved organic matter according to source using fluorescence signatures", Chemosphere, vol. 155, Jul. 2016, pp. 283-291, <http://dx.doi.org/10.1016/j.chemosphere.2016.04.061>.

Qingcai Chen et al., "Light Absorption and Excitation-Emission Fluorescence of Urban Organic Aerosol Components and Their Relationship to Chemical Structure", Environmental Science & Technology, vol. 50, Sep. 6, 2016, pp. 10859-10868, DOI: 10.1021/acs.est.6b02541.

* cited by examiner

| TYPE | SUBSTANCES INCLUDED IN REFERENCE SPECTRAL DATA SET |
|---|---|
| FOOD | PHENYLALANINE, TYROSINE, TRYPTOPHAN, ATP, CHLOROPHYLL, NADH, VITAMIN B2 |
| RIVER WATER/ TAP WATER | HUMIC ACID, FULVIC ACID, TRYPTOPHAN |
| INDUSTRIAL WASTEWATER | AMINO ACID, NADH |
| AEROSOL | NADH, CEDAR POLLEN (Cryj1, Cryj2), CYPRESS POLLEN (Chao1, Chao2) |

FIG. 7G

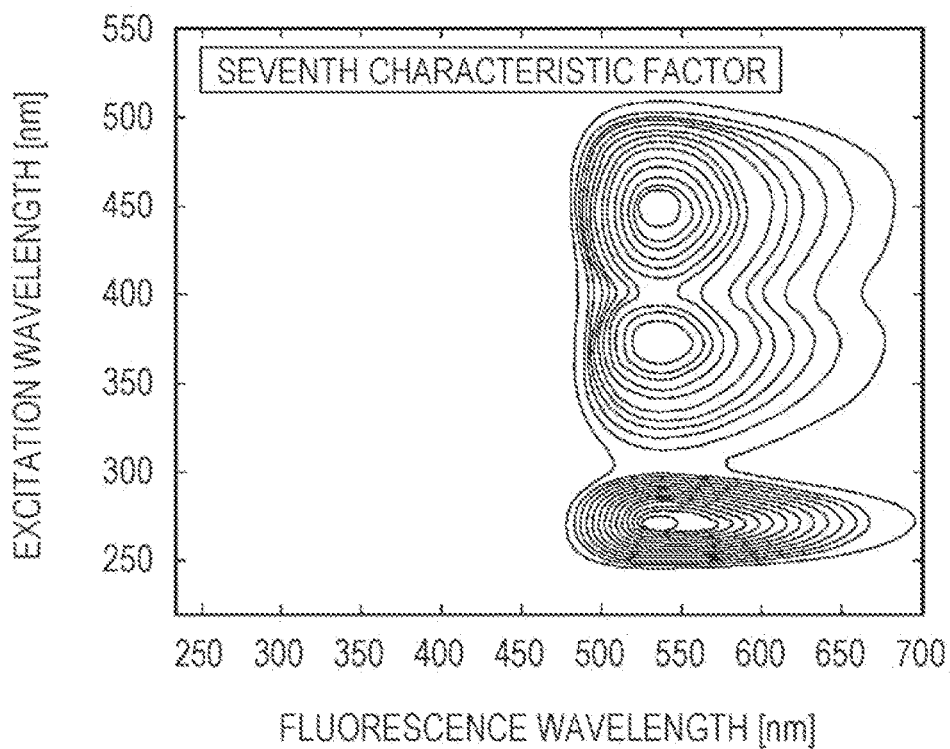

FIG. 8

| MEASURED SAMPLE | | SCORES FOR CORN |
|---|---|---|
| FIRST CHARACTERISTIC FACTOR | CORRESPONDING TO PHENYLALANINE | 0 |
| SECOND CHARACTERISTIC FACTOR | CORRESPONDING TO TYROSINE | 5.95 |
| THIRD CHARACTERISTIC FACTOR | CORRESPONDING TO TRYPTOPHAN | 16.7 |
| FOURTH CHARACTERISTIC FACTOR | CORRESPONDING TO ATP | 4.00 |
| FIFTH CHARACTERISTIC FACTOR | CORRESPONDING TO CHLOROPHYLL | 4.00 |
| SIXTH CHARACTERISTIC FACTOR | CORRESPONDING TO NADH | 40.0 |
| SEVENTH CHARACTERISTIC FACTOR | CORRESPONDING TO VITAMIN B2 | 12.0 |

COMPONENT ANALYSIS DEVICE AND COMPONENT ANALYSIS METHOD

BACKGROUND

1. Technical Field

The present disclosure relates to a component analysis device and a component analysis method.

2. Description of the Related Art

Recently, EEM (Excitation-Emission Matrix) is known as a method for analyzing the quality of river water and sewage treated water, food, and so on. For example, Japanese Patent No. 5985709 discloses a food analysis method utilizing data obtained by EEM (hereinafter referred to as "EEM data"). Furthermore, Jakob Christensen, et al., "Multivariate Autofluorescence of Intact Food Systems", Chemical Review, Vol. 106, No. 6 (2006) discloses, as a method for analyzing the EEM data, a technique utilizing PARAFAC (Parallel Factor Analysis) that is one type of chemometric analysis.

SUMMARY

In one general aspect, the techniques disclosed here feature a component analysis device including a data acquisition circuit that acquires spectral data of an analyte containing components, the spectral data being obtained by measuring a spectrum of the analyte with a sensor, a type acquisition circuit that acquires information indicating a type of the analyte, a storage that stores a reference spectral data set including multiple spectral data of substances each of which is estimated to be included in the analyte, the reference spectral data set corresponding to the type of the analyte, and an analysis circuit that performs a parallel factor analysis by using, as input data, the spectral data of the analyte and the reference spectral data set.

In another general aspect, the techniques disclosed here feature a component analysis method including acquiring spectral data of an analyte containing components, the spectral data being obtained by measuring a spectrum of the analyte, acquiring information indicating a type of the analyte, obtaining a reference spectral data set including multiple spectral data of substances each of which is estimated to be included in the analyte, the reference spectral data set corresponding to the type of the analyte, and performing a parallel factor analysis by using, as input data, the spectral data of the analyte and the reference spectral data set.

In still another general aspect, the above-described component analysis method can be implemented as a program instructing a computer to execute the component analysis method. Furthermore, the above-described component analysis method can be implemented as a non-transitory computer-readable recording medium storing the program.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7G illustrates three-dimensional spectral data of a seventh characteristic factor separated by PARAFAC;

FIG. 8 is a table illustrating scores corresponding to seven characteristic factors, the scores being obtained by the component analysis device according to the embodiment.

DETAILED DESCRIPTION

Figure 1:
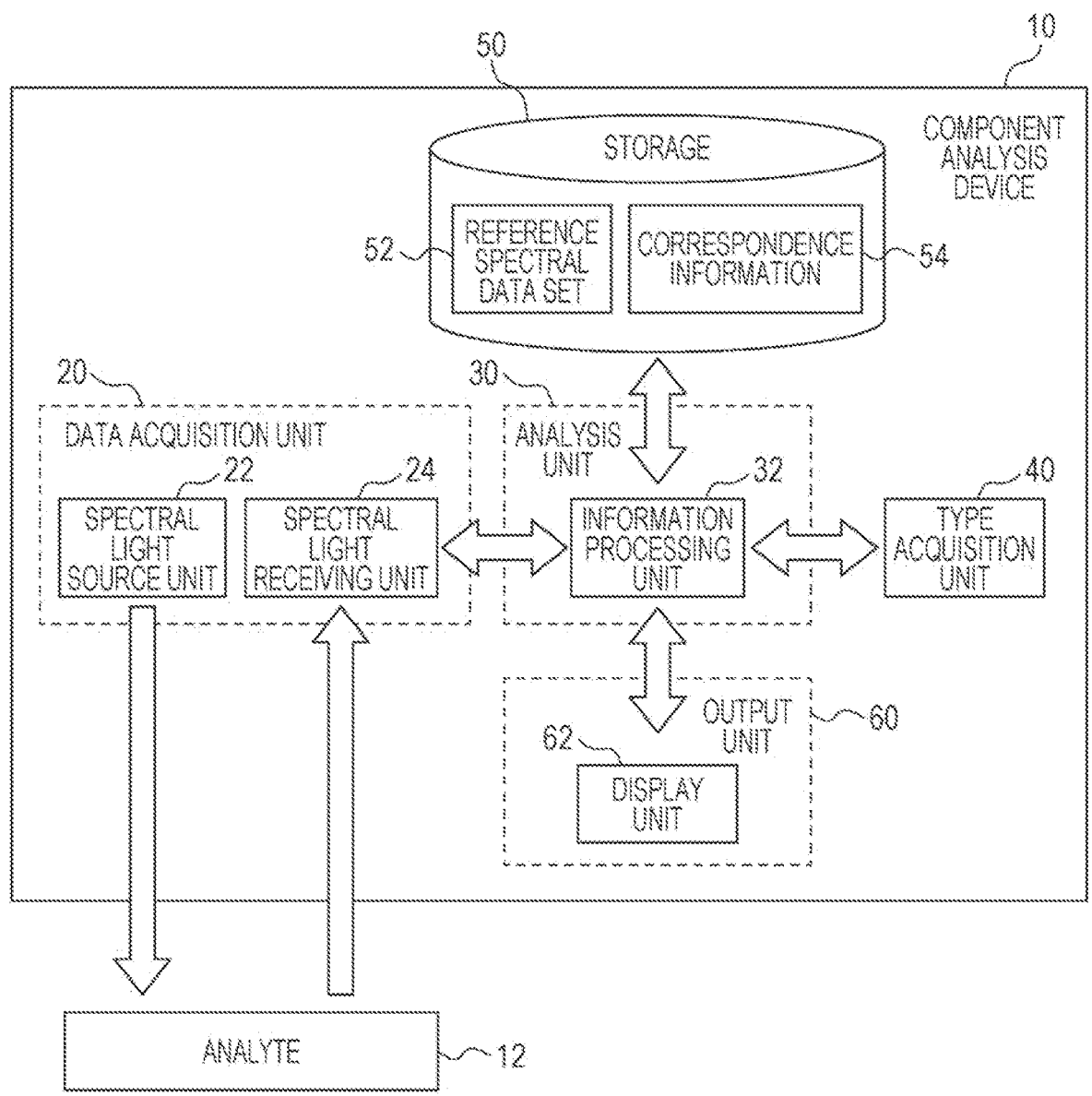
FIG. 1 is a block diagram illustrating a functional configuration of a component analysis device according to an embodiment.

Underlying Knowledge Forming Basis of the Present Disclosure

Regarding the related art described in "Description of the Related Art", the inventors have found the following problems.

A spectral fluorescence analysis represented by EEM is an analysis method capable of performing a component analysis with high accuracy because of utilizing fluorescence that is light specific to a substance. Furthermore, the spectral fluorescence analysis is an analysis method with about 1000 times higher accuracy than an absorbance analysis.

Meanwhile, food or river water, namely an analyte, usually contains multiple types of components. Thus EEM data is complicated because multiple types of components emit individual rays of light and multiple fluorescence spectra are superimposed.

According to PARAFAC, peaks of the superimposed fluorescence spectra can be separated from the complicated EEM data for each component exhibiting the same light emission behavior. By using information of the separated peaks, a quantitative analysis can be performed on the basis of the peak intensity of fluorescence, and a component analysis can be performed on the basis of the peak wavelength of fluorescence. In addition, an identification analysis can be realized by performing a principal component analysis.

However, in trying to separate the peaks by performing PARAFAC directly on the EEM data that is actually measured data, namely on actual sample data, the peaks cannot be properly separated in some cases. There may occur, for example, a case in which a minus peak is separated, or a case in which an expected peak cannot be separated. In order to properly perform the peak separated by PARAFAC, it is needed to set appropriate boundary conditions and so on, and to obtain preparatory data from many samples in advance. Hence the prior-art PARAFAC has a difficulty in performing the appropriate separation of the components.

The technique disclosed in the above-cited Japanese Patent No. 5985709 also needs to previously prepare database for each of foods to be analyzed.

In consideration of the above-described situations, non-limiting and exemplary embodiments provide a component analysis device and a component analysis method each of which can simply and accurately perform a component analysis of an analyte.

A component analysis device according to one aspect of the present disclosure includes a data acquisition circuit that acquires spectral data having been obtained by measuring a spectrum of the analyte containing multiple components with a sensor, and an analysis circuit that identifies the multiple components by performing a factor analysis of input data that is given as a combination of the spectral data acquired by the data acquisition circuit and at least one reference spectral data set read from a storage, the storage previously storing the at least one reference spectral data set representing spectra of the multiple substances.

With the above-described feature, since the factor analysis is performed on the input data including the reference spectral data set, the separation accuracy of characteristic factors can be increased. Furthermore, there is no necessity of preparing many data obtained by actual measurements, and separation of the components included in the spectral data can be performed with high accuracy. Thus, with the component analysis device according to this aspect, the component analysis of the analyte can be simply executed with high accuracy.

For example, the factor analysis may be a parallel factor analysis.

With the above-described feature, the component analysis of the analyte can be simply executed with high accuracy. For example, the number of the spectral data of the analyte may be M, the number of the multiple spectral data included in the reference spectral data set may be N, and the analysis circuit may perform the parallel factor analysis on (M+N) pieces of spectral data.

For example, the spectral data may be three-dimensional fluorescence spectral data.

With the above-described feature, since the so-called EEM data is utilized, the component analysis of, for example, food containing organic substances emitting fluorescence can be simply executed with high accuracy.

For example, the multiple substances may be each a substance emitting autofluorescence, and the at least one reference spectral data set may represent fluorescence spectra of the multiple substances.

With the above-described feature, the component analysis of, for example, the food containing the organic substances emitting autofluorescence can be simply executed with high accuracy.

For example, the multiple substances may be substances contained in food.

With the above-described feature, the component analysis of food or vomit can be performed. For example, It is possible to discriminate food and vomit. It is also possible to determine the presence or absence of the residue that is left after cleaning to remove the vomit. Therefore, the present disclosure can be further utilized to increase the efficiency of cleaning work and purification work.

For example, the multiple substances may be organic substances contained in tap water, river water, or industrial wastewater.

With the above-described feature, since the component analysis of river water before water purification treatment or tap water (namely, river water after the water purification treatment) is performed with high accuracy, whether a humic substance, amino acid, and so on are contained in the river water or the tap water can be determined with high accuracy. This makes it possible to evaluate the performance of the water purification treatment, namely whether the humic substance, the amino acid, and so on have been appropriately removed. In addition, the component analysis device according to one aspect of the present disclosure can be utilized to inspect the quality of river water.

Moreover, since the component analysis of industrial wastewater is performed with high accuracy, whether pollution treatment of the industrial wastewater has been appropriately performed can be determined with high accuracy. In a milk factory, for example, washing of milk bottles after use is performed, and washing water is discharged as industrial wastewater after being subjected to water purification treatment. By performing the component analysis of the washing water after the water purification treatment, it is possible to evaluate whether substances derived from microorganisms, such as amino acids, have been appropriately removed.

For example, the multiple substances may be aerosol particles or substances contained in aerosol particles.

With the above-described feature, since the component analysis of aerosol particles is performed with high accuracy, whether pollen and so on floating in air, for example, can be determined with high accuracy. It is hence possible to evaluate, for example, whether cleaning of air by an air cleaner has been appropriately performed.

For example, the component analysis device according to one aspect of the present disclosure may further include a type acquisition circuit that acquires information indicating a type of the analyte. The at least one reference spectral data set may include multiple reference spectral data sets. Each of the multiple reference spectral data sets may be determined in advance per type of the analyte. The analysis circuit may select, from among the multiple reference spectral data sets, the reference spectral data set corresponding to the type indicated by the information that has been acquired by the type acquisition circuit, and may perform the factor analysis by using, as the input data, the selected reference spectral data set and the spectral data.

With the above-described feature, since the number of types of analyzable analytes can be increased, the component analysis can be performed on various types of analytes.

For example, the component analysis device according to one aspect of the present disclosure may further include the above-mentioned storage.

With the above-described feature, even when communication environments are not ready, the component analysis of the analyte can be simply executed with high accuracy. Furthermore, since alteration, addition, update, and so on of the reference spectral data set stored in the storage can be made as required, the number of types of the analyzable analytes can be increased. In addition, the accuracy of the component analysis can be further increased.

A component analysis method according to one aspect of the present disclosure includes acquiring spectral data that has been obtained by measuring a spectrum of an analyte containing multiple components, and identifying the multiple components by performing a factor analysis of input data that is given as a combination of the spectral data and at least one reference spectral data set read from a storage, the storage previously storing the at least one reference spectral data set representing spectra of the multiple substances.

With the above-described feature, the component analysis of the analyte can be simply executed with high accuracy as in the case of the above-described component analysis device.

For example, the component analysis method according to one aspect of the present disclosure may further include acquiring information indicating a type of the analyte, the at least one reference spectral data set may include multiple reference spectral data sets, each of the multiple reference spectral data sets may be determined in advance per type of the analyte, and identifying the multiple substances may include selecting, from among the multiple reference spectral data sets, the reference spectral data set corresponding to the type indicated by the information that has been acquired by acquiring the information, and performing the factor analysis by using, as the input data, the selected reference spectral data set and the spectral data.

With the above-described feature, since the number of types of analyzable analytes can be increased, the component analysis can be performed on various types of analytes.

For example, the component analysis method according to one aspect of the present disclosure may further include measuring the spectrum of the analyte.

With the above-described feature, data obtained by actual measurement can be analyzed with high accuracy.

A program according to one aspect of the present disclosure is a program instructing a computer to execute the above-described component analysis method.

With the above-described feature, the component analysis of the analyte can be simply executed with high accuracy as in the case of the above-described component analysis device.

A non-transitory computer-readable recording medium according to one aspect of the present disclosure stores a program to execute a component analysis of an analyte, and when the program is executed by a computer, the computer executes acquiring spectral data that has been obtained by measuring a spectrum of the analyte containing multiple components, and identifying the multiple components by performing a factor analysis of input data that is given as a combination of the spectral data and at least one reference spectral data set read from a storage, the storage previously storing the at least one reference spectral data set representing spectra of multiple substances.

In the present disclosure, all or part of circuits, units, devices, members, or portions, or all or part of functional blocks in the block diagram may be implemented by one or more electronic circuits including a semiconductor device, an IC (Integrated Circuit), or a LSI (Large Scale Integration), for example. The IC or the LSI may be integrated on one chip or may be constituted by a combination of multiple chips. Although the term "IC" or "LSI" is used here, the name of that type of semiconductor device varies depending on a degree of integration, and it may also be called a system LSI, a VLSI (Very Large Scale Integration), or a ULSI (Ultra Large Scale Integration). A Field Programmable Gate Array (FPGA) that is programmable after manufacturing of the LSI, or a reconfigurable logic device in which connection relations in the LSI is reconfigurable or in which a circuit section in the LSI can be set up may also be used for the same purpose.

Moreover, functions or operations in all or part of the circuits, the units, the devices, the members, or the portions can be executed by software processing. In that case, the software is stored in one or more non-transitory computer-readable recording media, such as ROMs, optical disks, or hard disk drives. When the software is executed by a processor, the function specified by the relevant software is executed by the processor and peripheral devices. The system or the device may include one or more non-transitory computer-readable recording media on which the software is recorded, the processor, and other required hardware devices such as an interface.

Embodiments will be described in detail below with reference to the drawings.

It is to be noted that any of the embodiments described below represents a generic or specific example. Numerical values, shapes, materials, constituent elements, arrangement positions and connection forms of the constituent elements, steps, sequences of steps, and so on, which are described in the following embodiments, are merely illustrative, and they are not purported to limit the scope of the present disclosure. Among the constituent elements in the following embodiments, those ones other than the constituent elements not stated in independent claims, which define the most significant concepts, are described as optional constituent elements.

The drawings are not always exactly depicted in a strict sense. Throughout the drawings, substantially the same constituent elements are denoted by the same reference sings, and duplicate description of those constituent elements is omitted or simplified.

EMBODIMENTS

1. Configuration

First, a configuration of a component analysis device according to an embodiment is described below with reference to FIG. 1.

FIG. 1 is a block diagram illustrating a functional configuration of a component analysis device 10 according to the embodiment. As illustrated in FIG. 1, the component analysis device 10 includes a data acquisition unit 20 that is a data acquisition circuit, an analysis unit 30 that is an analysis circuit, a type acquisition unit 40 that is a type acquisition circuit, a storage 50, and an output unit 60.

The component analysis device 10 performs a component analysis of an analyte 12. The analyte 12 is, for example, food or vomit. In another example, the analyte 12 may be water such as tap water, river water, or industrial wastewater. In still another example, the analyte 12 may be aerosol particles floating in a space.

The analyte 12 contains multiple components. Each of the components is given as a substance emitting autofluorescence. The components are, for example, organic substances. When the components are irradiated with excitation light having a peak at a certain wavelength, each component emits fluorescence having a peak at a certain wavelength. A combination of the peak wavelength of the excitation light and the peak wavelength of the fluorescence are specific to each component. Accordingly, the component can be identified by determining the combination of the peak wavelength of the excitation light and the peak wavelength of the fluorescence.

The data acquisition unit 20 acquires spectral data obtained by measuring a spectrum of the analyte 12. The spectral data obtained by the data acquisition unit 20 is three-dimensional fluorescence spectral data. The three-dimensional fluorescence spectral data is the so-called EEM data, namely three-dimensional data with three axes representing an excitation wavelength, a fluorescence wavelength, and fluorescence intensity. The EEM data is also called a fluorescence fingerprint. The excitation wavelength is the wavelength of the excitation light with which the analyte 12 is irradiated. The fluorescence wavelength is the wavelength of the fluorescence emitted from the analyte 12.

The EEM data is produced with measurement of the three-dimensional fluorescence spectrum. More specifically, the EEM data is obtained by measuring a fluorescence spectrum per excitation wavelength while continuously changing the wavelength of the excitation light with which the analyte 12 is irradiated. For example, when the analyte 12 is corn, the EMM data of corn, illustrated in FIG. 2, is obtained.

Figures 2, 3:
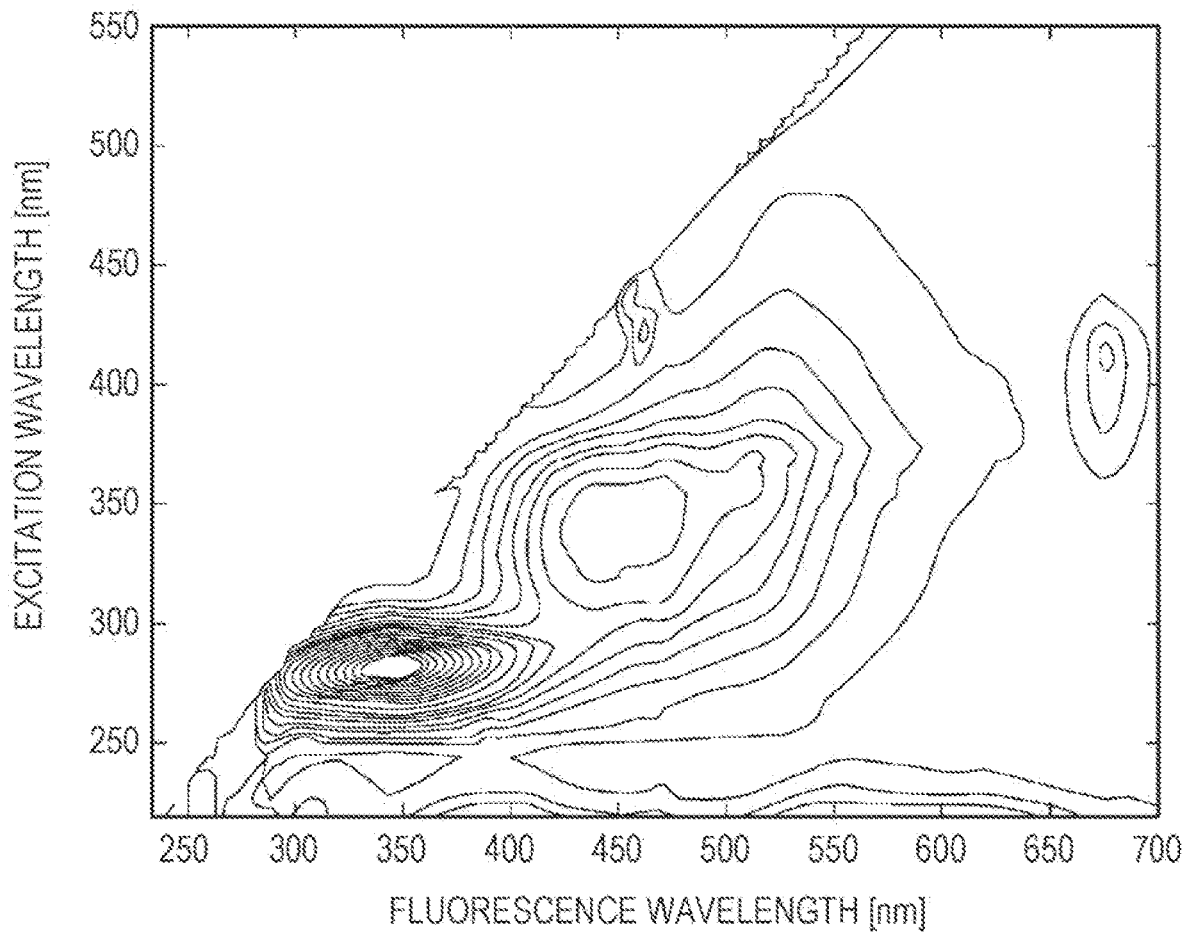
FIG. 2 illustrates EEM data of corn.
FIG. 3 is a table illustrating an example of correspondence information stored in a storage.

FIG. 2 illustrates the EEM data of corn. More specifically, FIG. 2 illustrates the EEM data obtained when a sample prepared by adding a predetermined amount of water to freeze-dried corn is used as the analyte 12.

In FIG. 2, the horizontal axis indicates the fluorescence wavelength [unit: nm], and the vertical axis indicates the excitation wavelength [unit: nm]. The fluorescence wavelength is the wavelength of fluorescence emitted from corn. The excitation wavelength is the wavelength of the excitation light with which the corn is irradiated. FIG. 2 represents isointensity lines each continuously connecting the coordinates in a two-dimensional coordinate system at which the fluorescence intensity is equal. Taking corn as an example, a peak of the fluorescence intensity is obtained with a combination of the excitation wavelength of about 280 nm and the fluorescence wavelength of about 340 nm.

The data acquisition unit 20 is realized with, for example, an optical unit. More specifically, as illustrated in FIG. 1, the data acquisition unit 20 includes a spectral light source unit 22 and a spectral light receiving unit 24.

The spectral light source 22 is a light source emitting the excitation light that has been dispersed into wavelength components. More specifically, the spectral light source unit 22 emits multiple rays of excitation light having peak wavelengths different from one another. The multiple rays of excitation light are each, for example, pulse light. In an example, the spectral light source unit 22 emits the multiple rays of excitation light in sequence with which the analyte 12 is irradiated.

The spectral light source unit 22 includes, for example, a light source that emits light with a wide wavelength band, such as white light, and multiple band pass filters (BPFs) that are disposed on a light emitting side of the light source. The light source is, for example, a discharge lamp such as a halogen lamp, or a solid light emitting element such as an LED (Light Emitting Diode) or a laser element. The BPFs have different pass bands, and each BPF sufficiently attenuates light of wavelengths other than its pass band. A half-width of the pass band of the BPF is, for example, greater than or equal to 10 nm and smaller than or equal to 50 nm. The pass bands of the BPFs do not overlap with each other. In an example, the spectral light source unit 22 emits the multiple rays of excitation light in sequence by switching, per constant time interval, the BPF that is to be positioned on the light emitting side of the light source. As a result, the analyte 12 can be irradiated with the excitation light having the excitation wavelength that is continuously changed.

A combination of a diffraction grating or a prism and a slit may be used instead of the BPFs. The excitation wavelength can be continuously changed by rotating the diffraction grating or the prism such that only light of a particular wavelength passes through the slit.

The spectral light receiving unit 24 disperses fluorescence emitted from the analyte 12 upon irradiation of the analyte 12 with the excitation light, and receives the fluorescence that has been dispersed into wavelength components. More specifically, the spectral light receiving unit 24 receives rays of the fluorescence having passed through multiple light receiving bands of different wavelengths.

The spectral light receiving unit 24 includes, for example, a photoelectric transducer for converting the received light to an electrical signal and outputting the electrical signal, and multiple BPFs that are disposed on a light incident side of the photoelectric transducer. The photoelectric transducer is, for example, a photodiode and outputs an electrical signal with signal intensity corresponding to the intensity of the received light. The photoelectric transducer may be a PMT (Photomultiplier Tube). The BPFs have different pass bands, and each BPF sufficiently attenuates light of wavelengths other than its pass band. A half-width of the pass band of the BPF is, for example, greater than or equal to 5 nm and smaller than or equal to 50 nm. The pass bands of the BPFs do not overlap with each other.

For example, the spectral light receiving unit 24 receives the fluorescence in each of the light receiving bands by sequentially changing, per constant time interval, the BPF that is to be positioned on the light incident side of the photoelectric transducer. In an example, the spectral light receiving unit 24 switches the BPFs from one to another during a period in which the analyte is irradiated with one ray of the excitation light. As a result, per excitation wavelength, the fluorescence intensity in each of the light receiving bands can be obtained and the EEM data can be produced.

The spectral light receiving unit 24 may include multiple photoelectric transducers corresponding to the multiple BPFs in a one-to-one relation. In this case, multiple rays of the fluorescence in the individual light receiving bands can be received at the same time, and a time required to measure the fluorescence spectrum can be shortened.

The spectral light receiving unit 24 may be an image sensor including multiple photoelectric transducers that are arrayed in a two-dimensional pattern. In this case, since the EEM data is obtained per photoelectric transducer, the fluorescence can be two-dimensionally observed. Therefore, the component analysis of the analyte 12 existing over a wide region in a space can be performed at a time.

The data acquisition unit 20 may be realized with an input interface or a communication interface accepting data that is output from a measurement device measuring the three-dimensional fluorescence spectrum. In other words, the component analysis device 10 may not need to include the spectral light source unit 22 and the spectral light receiving unit 24, and another measurement device may include the spectral light source unit 22 and the spectral light receiving unit 24.

The analysis unit 30 obtains, as input data, the spectral data acquired by the data acquisition unit 20 and a reference spectral data set 52 read out from the storage 50, and identifies multiple components included in the spectral data by performing a factor analysis of the input data. More specifically, the factor analysis is a parallel factor analysis (PARAFAC). PARAFAC is performed in accordance with the following formula (1).

$$x_{ijk} = \sum_{f=1}^{F} a_{if} b_{jf} c_{kf} + e_{ijk} \quad (i=1,2,\ldots,I, j=1,2,\ldots,J, k=1,2,\ldots,K) \quad (1)$$

In the formula (1), $x_{ijk}$ denotes the fluorescence intensity of input data k with respect to a combination of an excitation wavelength i and a fluorescence wavelength j. I, J and K denote respectively the number of rays of the excitation light, the number of fluorescence receiving bands, and the number of input data. F corresponds to a maximum number of characteristic factors separated from $x_{ijk}$, namely the number of components included in $x_{ijk}$. Thus the analysis unit 30 identifies each of the number f of components by performing PARAFAC.

Furthermore, $a_{if}$, $b_{jf}$ and $c_{kf}$ correspond respectively to concentrations of an excitation spectrum, the fluorescence spectrum, and the input data for a component f. In other words, a term denoted by $a_{if} b_{jf} c_{kf}$ corresponds to the three-dimensional spectral data of the component f separated by PARAFAC, namely three-dimensional spectral data of the f-th characteristic factor. Moreover, $e_{ijk}$ is an independent factor not depending on the excitation spectrum and the fluorescence spectrum. Thus $e_{ijk}$ corresponds to the residual that is left after separating the component f by PARAFAC.

In this embodiment, the analysis unit 30 identifies the component contained in the analyte 12 on the basis of a score of the f-th characteristic factor that has been separated. The score of the f-th characteristic factor is expressed by $a_{if} b_{jf} c_{kf}$ and is automatically calculated by performing PARAFAC. In this embodiment, the score of the f-th characteristic factor is calculated per spectral data included in the input data. The analysis unit 30 converts the score per spectral data in such a manner that a maximum one among all the scores of the f-th characteristic factor becomes 100.

The analysis unit 30 compares the score and a predetermined threshold for each characteristic factor. When the score of the characteristic factor exceeds the threshold, the analysis unit 30 determines that the component corresponding to the relevant characteristic factor is the component contained in the analyte 12. When the score of the characteristic factor is less than or equal to the threshold, the analysis unit 30 determines that the component corresponding to the relevant characteristic factor is not contained in the analyte 12. The threshold is 0, for example, but it is not limited to 0.

The analysis unit 30 is realized with, for example, software executed by a processor or the like. In another example, the analysis unit 30 may be realized with hardware such as an electronic circuit including multiple circuit elements. More specifically, as illustrated in FIG. 1, the analysis unit 30 includes an information processing unit 32.

The information processing unit 32 is, for example, a microcomputer. More specifically, the information processing unit 32 includes a signal processing circuit for processing signals output from the spectral light receiving unit 24, a nonvolatile memory in which programs are stored, a volatile memory that is a temporary storage area used to execute the programs, an input/output port, and a processor for executing the programs.

The type acquisition unit 40 acquires type information indicating the type of the analyte 12. The type acquisition unit 40 is realized with, for example, an input device such as a touch sensor on a touch panel display, a keyboard, or a mouse. The type acquisition unit 40 acquires the type information by accepting a user operation.

For example, the type acquisition unit 40 acquires the type information by presenting multiple candidates for the type of the analyte 12 to a user, and by prompting the user to select one among the presented candidates. The candidates are multiple types that are included in correspondence information listed in FIG. 3, for example. The type acquisition unit 40 may cause the user to input the type of the analyte 12 by, for example, text input or voice input.

The storage 50 stores the reference spectral data set 52 in advance. In this embodiment, the correspondence information 54 is further stored in the storage 50. The reference spectral data set 52 and the correspondence information 54 may be changeable, as required, by addition, deletion, update, or the like. The storage 50 is realized with, for example, a HDD (Hard Disk Drive) or a semiconductor memory.

The reference spectral data set 52 represents spectra of multiple substances that have been prepared in advance. More specifically, the reference spectral data set 52 represents fluorescence spectra of multiple substances. The reference spectral data set 52 is stored in the storage 50. In this embodiment, the reference spectral data set 52 having been previously determined for each type of the analyte 12 is stored in the storage 50.

The multiple substances are, for example, substances emitting autofluorescence. The multiple substances include substances that are previously estimated to be contained in the analyte 12, namely estimated characteristic factors. Alternatively, the multiple substances may include a substance that is expected to be not contained in the analyte 12. As illustrated in FIG. 3, the substances included in the reference spectral data set 52 are determined in advance for each type of the analyte 12.

FIG. 3 is a table illustrating an example of the correspondence information 54 stored in the storage 50. The correspondence information 54 represents correspondence relations between the types of the analytes 12 and the multiple substances included in the reference spectral data set 52.

As illustrated in FIG. 3, when the analyte 12 is food, the reference spectral data set 52 includes spectral data of seven substances, namely phenylalanine, tyrosine, tryptophan, ATP (adenosine triphosphate), chlorophyll, NADH (nicotinamide adenine dinucleotide), and vitamin B2. When the analyte 12 is river water or tap water, the reference spectral data set 52 includes spectral data of three substances, namely humic acid, fulvic acid, and tryptophan. When the analyte 12 is industrial wastewater, the reference spectral data set 52 includes spectral data of two substances, namely amino acid and NADH.

When the analyte 12 is aerosol, the reference spectral data set 52 includes spectral data of three substances, namely NADH, cedar pollen, and cypress pollen. NADH is an example of substances that are biologically derived and contained in aerosol particles. The cedar pollen and the cypress pollen are each an example of the aerosol particles.

The reference spectral data set 52 may include spectral data of two substances instead of the cedar pollen, namely Cryj1 and Cryj2 contained in the cedar pollen. Cryj1 and Cryj2 are main allergens of the cedar pollen. Similarly, the reference spectral data set 52 may include spectral data of two substances instead of the cypress pollen, namely Chao1 and Chao2 contained in the cypress pollen. Chao1 and Chao2 are main allergens of the cypress pollen.

The correspondence relations illustrated in FIG. 3 are merely one example. The types and the numbers of substances included in each reference spectral data set 52 are not limited to particular ones. The substances included in the reference spectral data set 52 for food may be selected including, for example, collagen or vitamin such as vitamin A or folic acid. The substances included in the reference spectral data set 52 for aerosol may be selected including, for example, aerosol particles and substances contained in the aerosol particles. In an example, the reference spectral data set 52 for aerosol may include the spectral data of cedar pollen, Cryj1, and Cryj2.

FIGS. 4A to 4G illustrate spectral data of the multiple substances included in the reference spectral data set 52 that is used when the analyte 12 is food. More specifically, the FIGS. 4A to 4G illustrate respectively EEM data of phenylalanine, tyrosine, tryptophan, ATP, chlorophyll, NADH, and vitamin B2. As illustrated in FIGS. 4A to 4G, the combination of the excitation wavelength and the fluorescence wavelength when the fluorescence intensity takes a peak value is specific to each of the substances.

The output unit 60 outputs the analysis result obtained by the analysis unit 30. More specifically, the analysis result is the result of the parallel factor analysis and is information to identify the components included in the EEM data that has been acquired by the data acquisition unit 20. The analysis result is, for example, the name of each of the components included in the EEM data. The component indicated by the analysis result corresponds to the component contained in the analyte 12.

The output unit 60 includes a display unit 62 for displaying, for example, an image that represents the analysis result. The display unit 62 is a liquid crystal display device, an organic EL (Electroluminescence) display device, or the like, but it is not limited to such an example.

The output unit 60 may further include a speaker for outputting the analysis result by voice. In addition, the output unit 60 may include an output interface or a communication interface for outputting, to an external device, a signal that indicates the analysis result.

2. Operation (Component Analysis Method)

An operation (component analysis method) of the component analysis device 10 according to this embodiment will be described below with reference to FIGS. 5 and 6.

Figure 5:
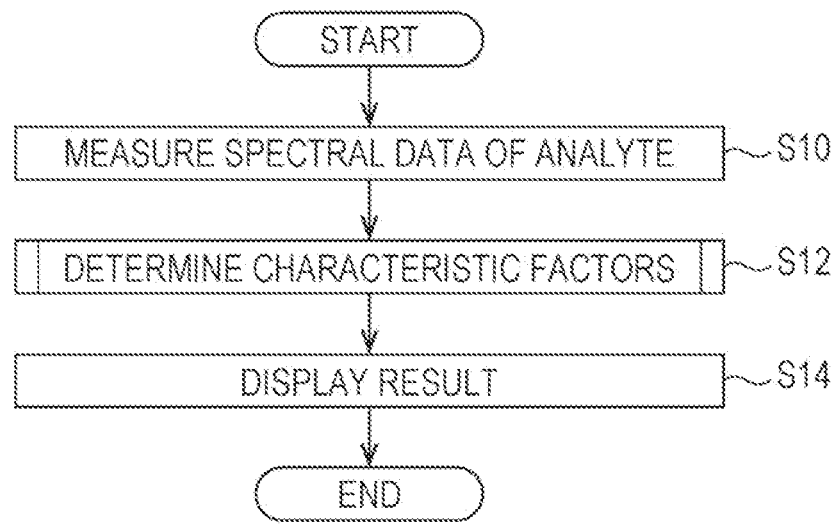
FIG. 5 is a flowchart illustrating an operation of the component analysis device according to the embodiment.
Figure 6:
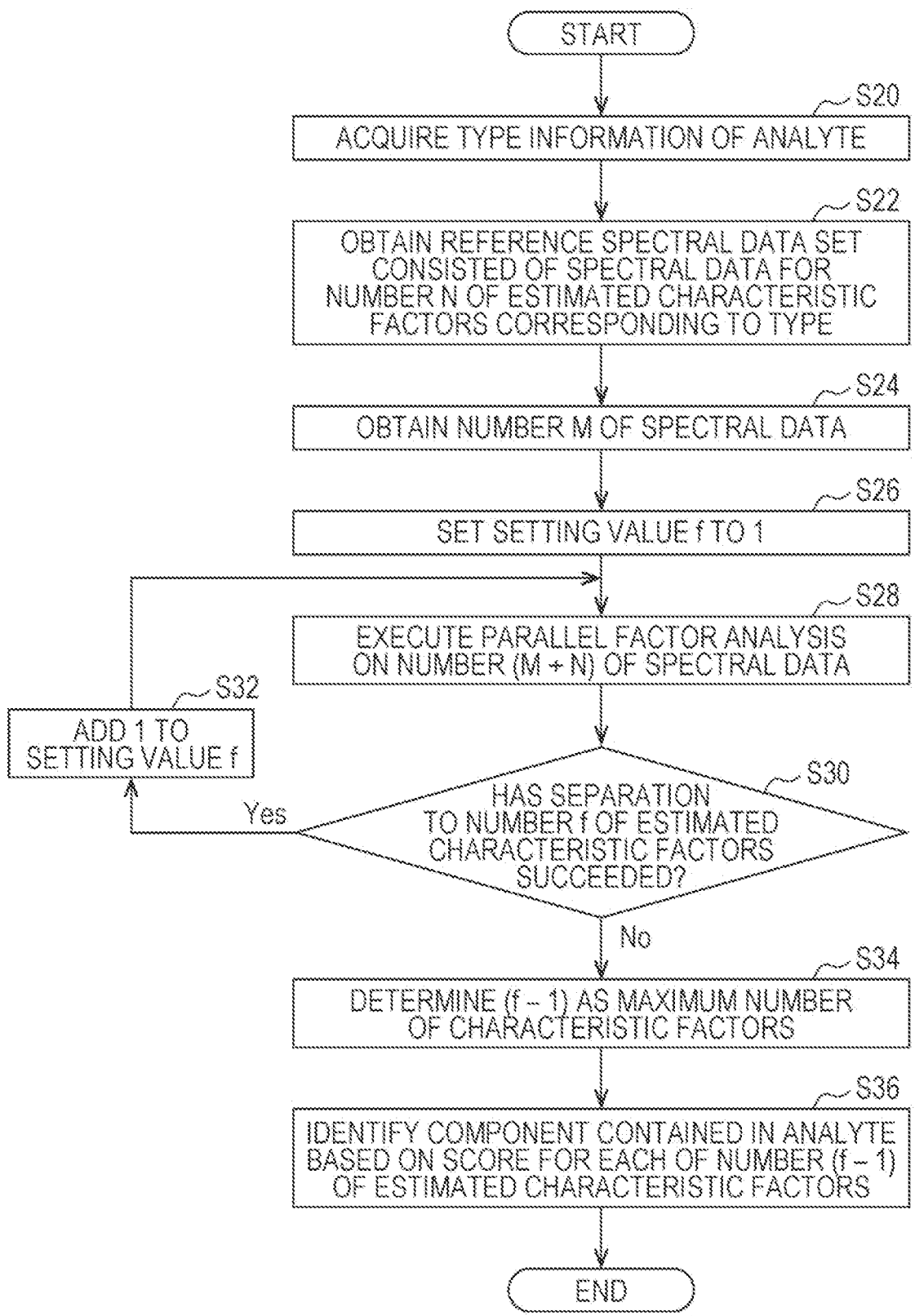
FIG. 6 is a flowchart illustrating a process of determining characteristic factors in the operation of the component analysis device according to the embodiment.

FIG. 5 is a flowchart illustrating the operation of the component analysis device 10 according to the embodiment. FIG. 6 is a flowchart illustrating a process of determining characteristic factors in the operation of the component analysis device 10 according to the embodiment. More specifically, FIG. 6 illustrates details of step S12 in FIG. 5.

First, as illustrated in FIG. 5, the data acquisition unit 20 measures spectral data of the analyte 12 (S10). More specifically, the data acquisition unit 20 measures a three-dimensional fluorescence spectrum of the analyte 12 and acquires EEM data as the spectral data. More specifically, the spectral light source unit 22 emits the excitation light while continuously varying the excitation wavelength, and the spectral light receiving unit 24 receives the fluorescence emitted from the analyte 12 for each of the light receiving bands, thereby measuring the three-dimensional fluorescence spectrum. One set of EEM data is obtained by one cycle of measurement. Multiple sets of EEM data may be obtained by repeating the measurement plural times. Here, the number of obtained EEM data is assumed to be M. M is a natural number and may be 1.

Then, the analysis unit 30 determines the components, namely the characteristic factors, included in the EEM data that has been acquired by the data acquisition unit 20 (S12). More specifically, as illustrated in FIG. 6, the type acquisition unit 40 first acquires the type information of the analyte 12 (S20). For example, the type acquisition unit 40 acquires the type information by prompting the user to input the type of the analyte 12 that has been measured in step S10.

Then, the analysis unit 30 obtains the reference spectral data set 52 that corresponds to the type indicated by the type information and that is made up of spectral data for the number N of estimated characteristic factors (S22). More specifically, the analysis unit 30 refers to the correspondence information 54 stored in the storage 50, determines the number N of substances that are included in the reference spectral data set 52 corresponding to the type indicated by the type information, and reads the spectral data for the number N of determined substances from the storage 50. Here, N is a natural number greater than or equal to 2.

Then, the analysis unit 30 obtains the number M of spectral data that have been acquired by the data acquisition unit 20 (S24). Furthermore, the analysis unit 30 sets a setting value f for use in the parallel factor analysis to 1 (S26). The setting value corresponds to the number of characteristic factors separated by the parallel factor analysis.

Then, the analysis unit 30 handles, as the input data, the reference spectral data set consisted of the number M of spectral data that have been obtained by the measurement using a sensor, and the spectral data for the number N of estimated characteristic factors. In other words, the analysis unit 30 executes the parallel factor analysis (PARAFAC) on the input data, namely the number (M+N) of spectral data (S28). If separation to the number f of characteristic factors has succeeded as a result of executing PARAFAC (Yes in S30), the analysis unit 30 adds 1 to the setting value f (S32) and executes PARAFAC again in accordance with the setting value f that has become 2 (S28). PARAFAC is repeatedly executed until the separation to the number f of characteristic factors does not succeed.

If the separation to the number f of characteristic factors has not succeeded (No in S30), the analysis unit 30 determines (f−1) as a maximum number of the characteristic factor (S34). In other words, the analysis unit 30 determines the maximum number of characteristic factors for which the separation has succeeded.

Then, the analysis unit 30 identifies the components contained in the analyte 12 on the basis of the individual scores of the number (f−1) of characteristic factors (S36). More specifically, the analysis unit 30 compares each of the scores with the threshold and identifies, as the component of the analyte 12, the component corresponding to the characteristic factor that exceeds the threshold.

After the identification result has been obtained, the display unit 62 displays the result as illustrated in FIG. 5 (S14). For example, the display unit 62 displays the result by listing the names of the components contained in the analyte 12. In another example, the display unit 62 may display the spectral data for each of the characteristic factors having been separated by PARAFAC, and the score for each of the characteristic factors.

3. Analysis Result

The following description is made about the result of performing the parallel factor analysis according to this embodiment using the spectral data illustrated in FIG. 2, which was obtained by the actual measurement. PARAFAC was executed by using, for example, Chemometrics Software Solo made by Eigenvector Research, Inc.

Because the analyte 12 was corn, namely food, the spectral data of seven substances of phenylalanine, tyrosine, tryptophan, ATP, chlorophyll, NADH, and vitamin B2, listed in FIG. 3, were used as the reference spectral data set. More specifically, eight spectral data in total, namely one spectral data illustrated in FIG. 2 and seven spectral data illustrated in FIGS. 4A to 4G, were used as the input data to execute PARAFAC.

As a result, separation to seven characteristic factors in total, namely the first to seventh characteristic factors illustrated in FIGS. 7A to 7G, succeeded. FIGS. 7A to 7G illustrate three-dimensional spectral data of the first to seventh characteristic factors that were separated by PARAFAC.

Figure 4A:
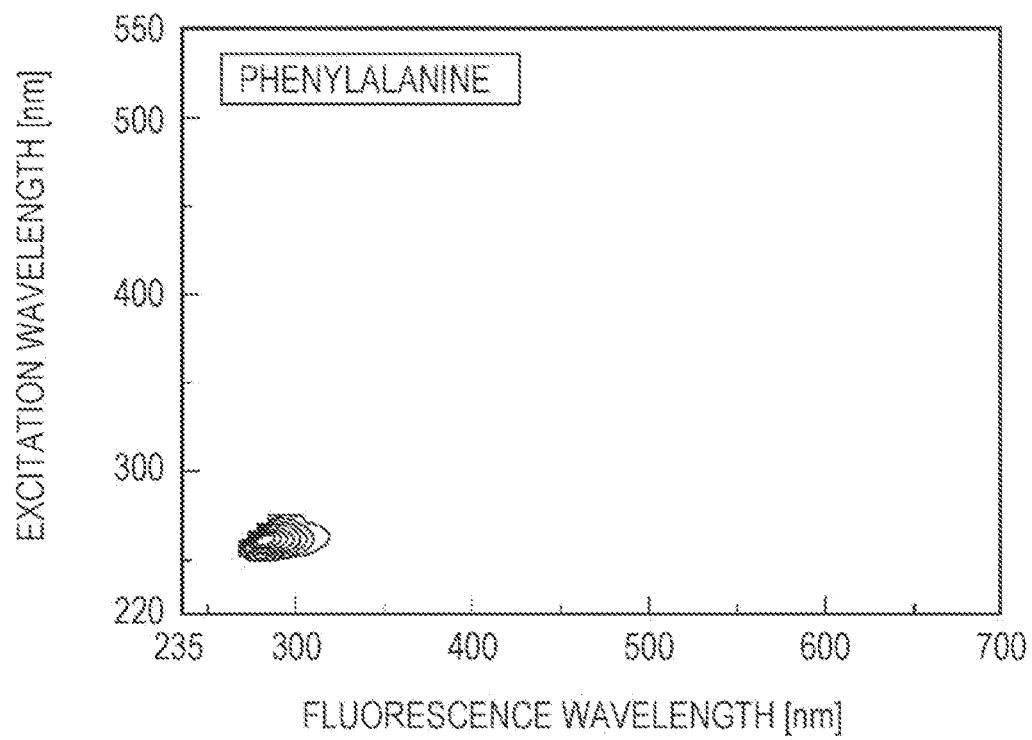
FIG. 4A illustrates EEM data of phenylalanine.
Figure 4B:
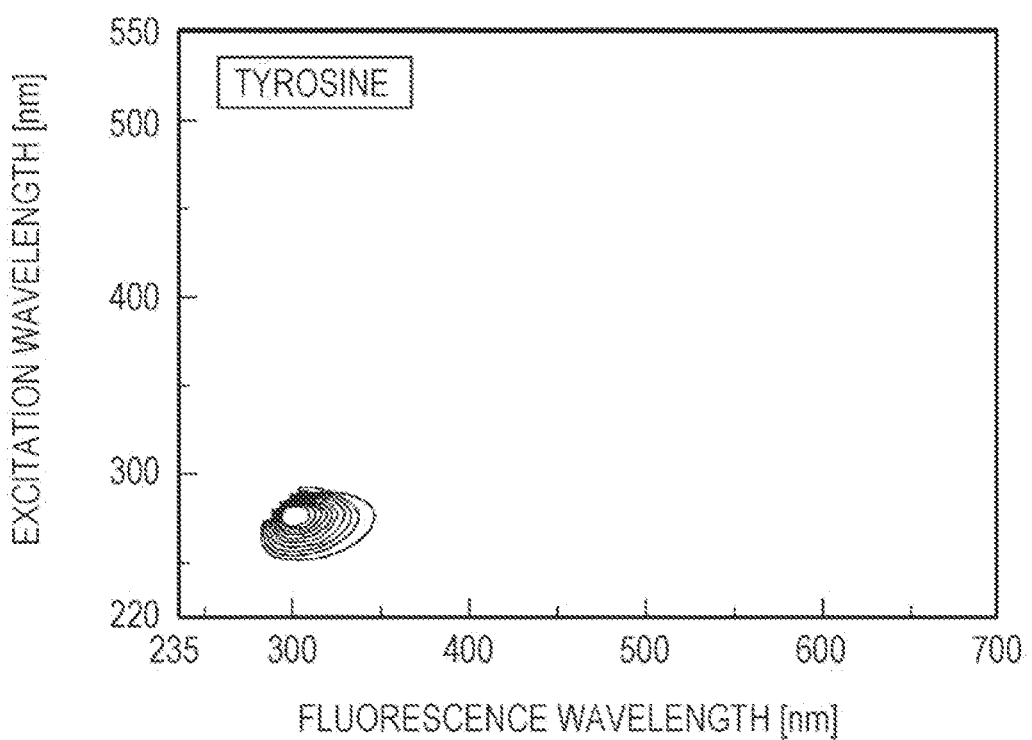
FIG. 4B illustrates EEM data of tyrosine.
Figure 4C:
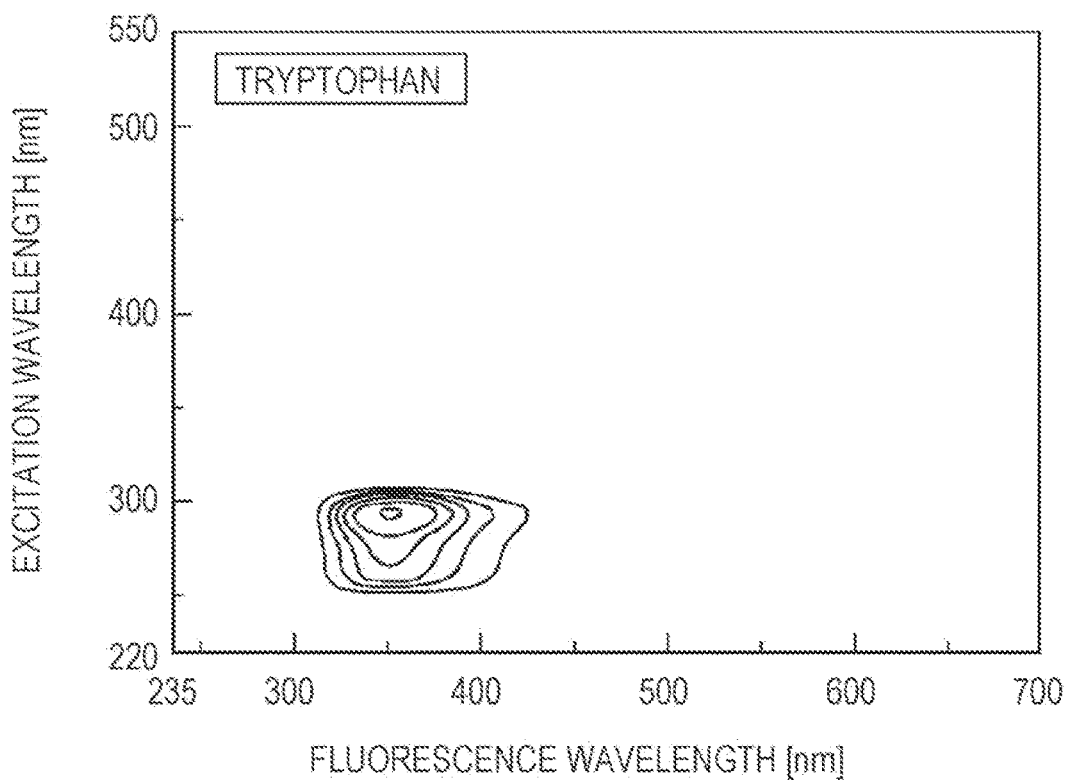
FIG. 4C illustrates EEM data of tryptophan.
Figure 4D:
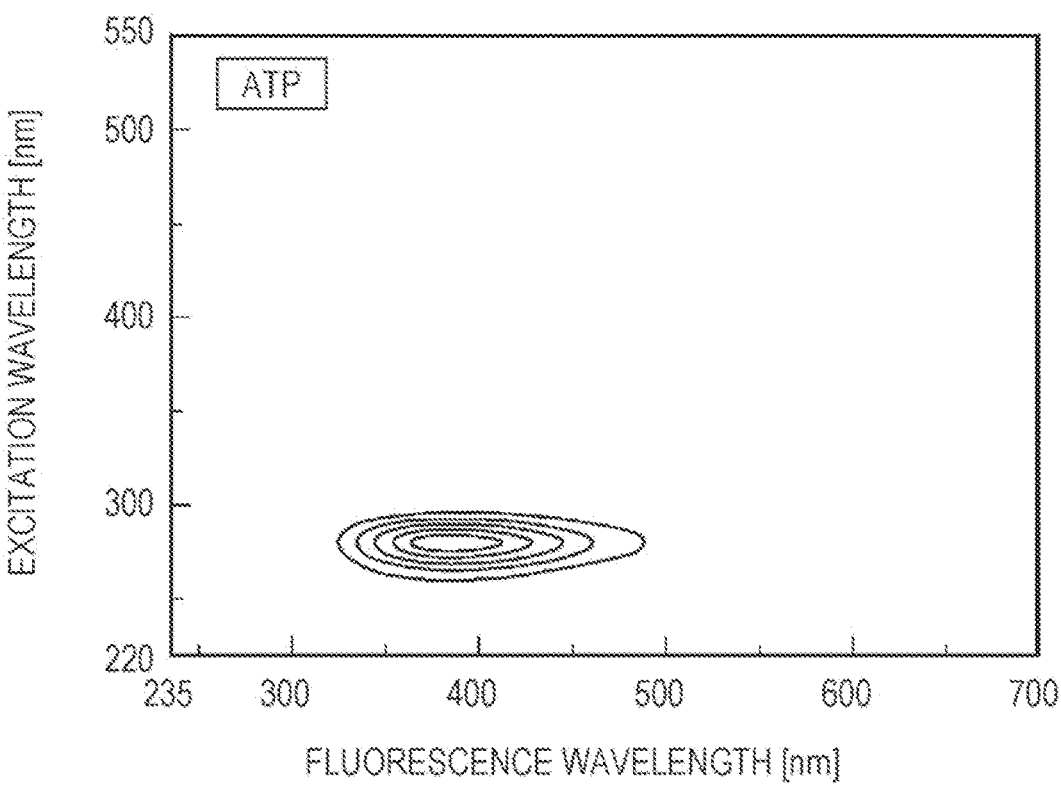
FIG. 4D illustrates EEM data of ATP.
Figure 4E:
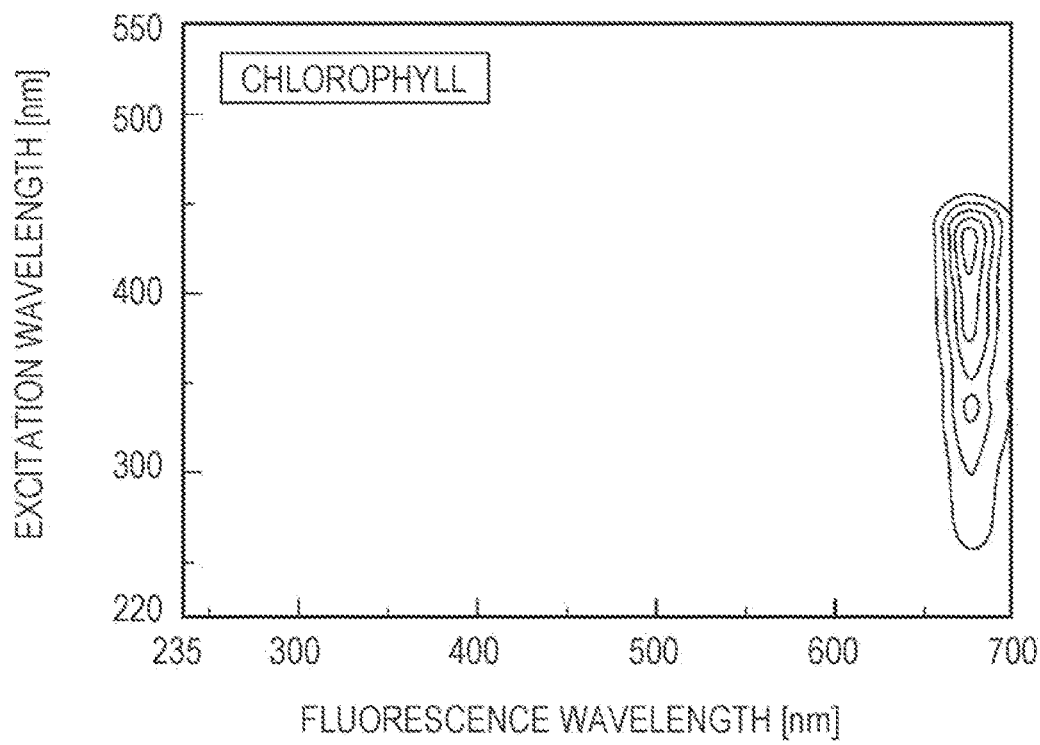
FIG. 4E illustrates EEM data of chlorophyll.
Figure 4F:
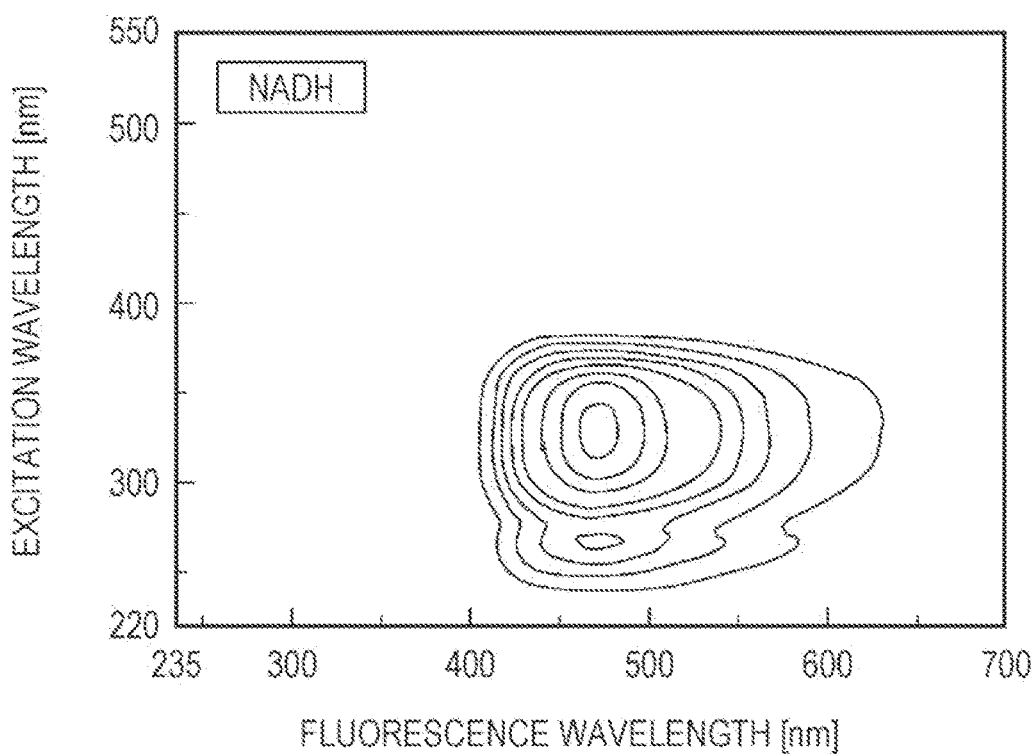
FIG. 4F illustrates EEM data of NADH.
Figure 4G:
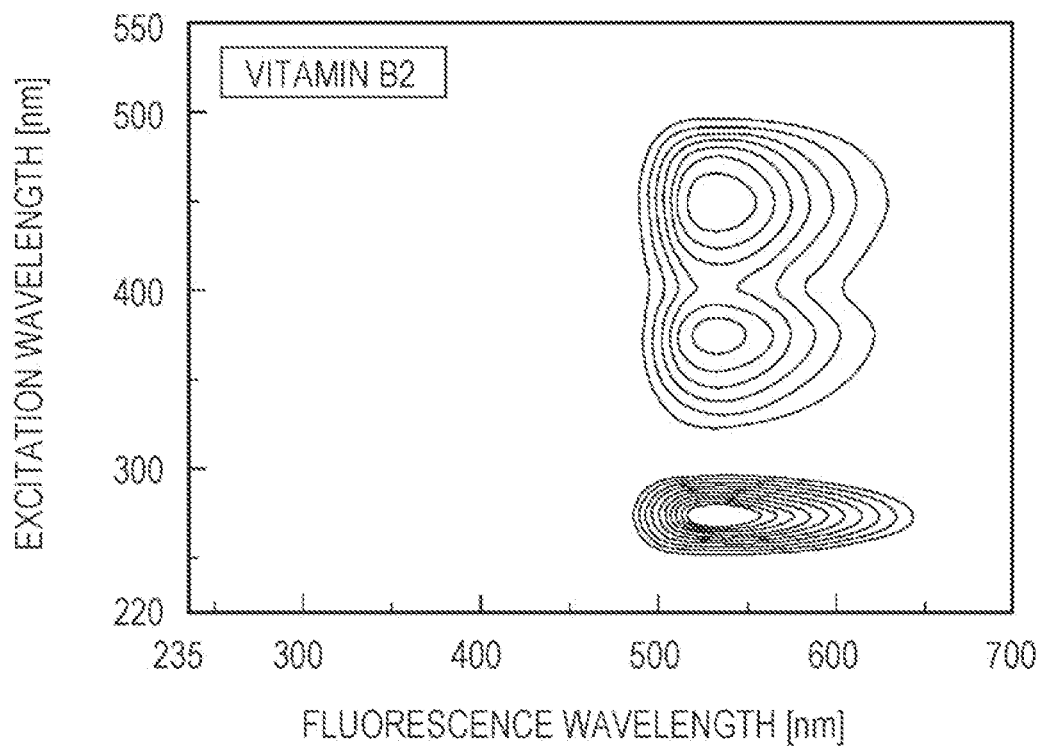
FIG. 4G illustrates EEM data of vitamin B2.
Figure 7A:
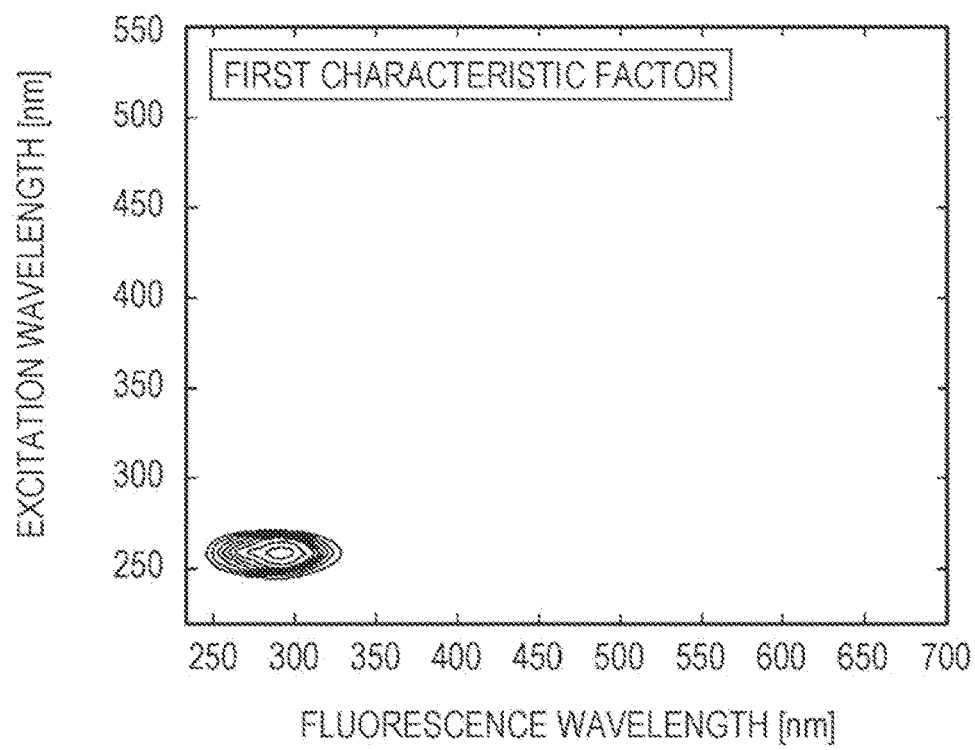
FIG. 7A illustrates three-dimensional spectral data of a first characteristic factor separated by PARAFAC.

Comparing, for example, the spectral data of the first characteristic factor illustrated in FIG. 7A and the spectral data of phenylalanine illustrated in FIG. 4A, it is seen that both the spectral data are similar. In other words, to which one of the multiple spectral data included in the input data the first characteristic factor corresponds can be determined on the basis of the scores of the first characteristic factor with respect to the individual spectral data included in the input data. More specifically, it is determined that the first characteristic factor corresponds to the spectral data for which a maximum one among the scores of the first characteristic factor has been obtained.

Regarding the second to seventh characteristic factors, the substance to which each characteristic factor corresponds can be determined in a similar manner on the basis of the scores for each of the characteristic factors. More specifically, the second characteristic factor illustrated in FIG. 7B corresponds to tyrosine illustrated in FIG. 4B. The third characteristic factor illustrated in FIG. 7C corresponds to tryptophan illustrated in FIG. 4C. The fourth characteristic factor illustrated in FIG. 7D corresponds to ATP illustrated in FIG. 4D. The fifth characteristic factor illustrated in FIG. 7E corresponds to chlorophyll illustrated in FIG. 4E. The sixth characteristic factor illustrated in FIG. 7F corresponds to NADH illustrated in FIG. 4F. The seventh characteristic factor illustrated in FIG. 7G corresponds to vitamin B2 illustrated in FIG. 4G.

FIG. 8 is a table illustrating scores corresponding to the seven characteristic factors, the scores being obtained by the component analysis device 10 according to the embodiment. As mentioned above, the scores are automatically calculated with the analysis unit 30 executing PARAFAC. Although FIG. 8 illustrates only the case in which the input data is the spectral data of corn, the scores are calculated for each of the characteristic factors with respect to the eight input data. The scores are indicated by values on an assumption that a maximum score value is 100.

Figure 7B:
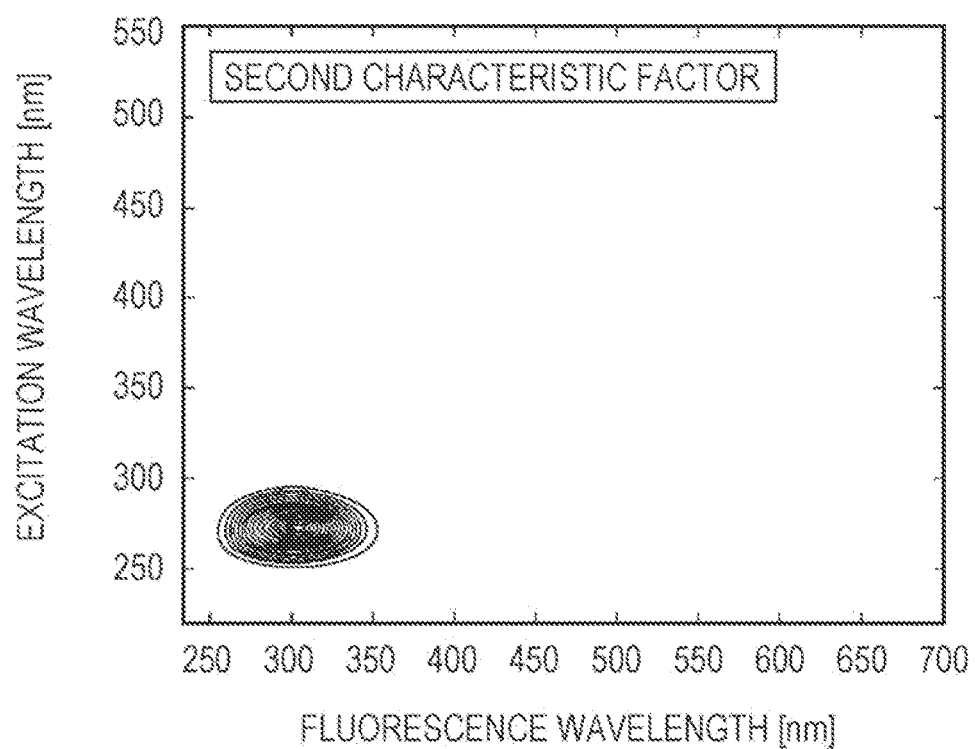
FIG. 7B illustrates three-dimensional spectral data of a second characteristic factor separated by PARAFAC.
Figure 7C:
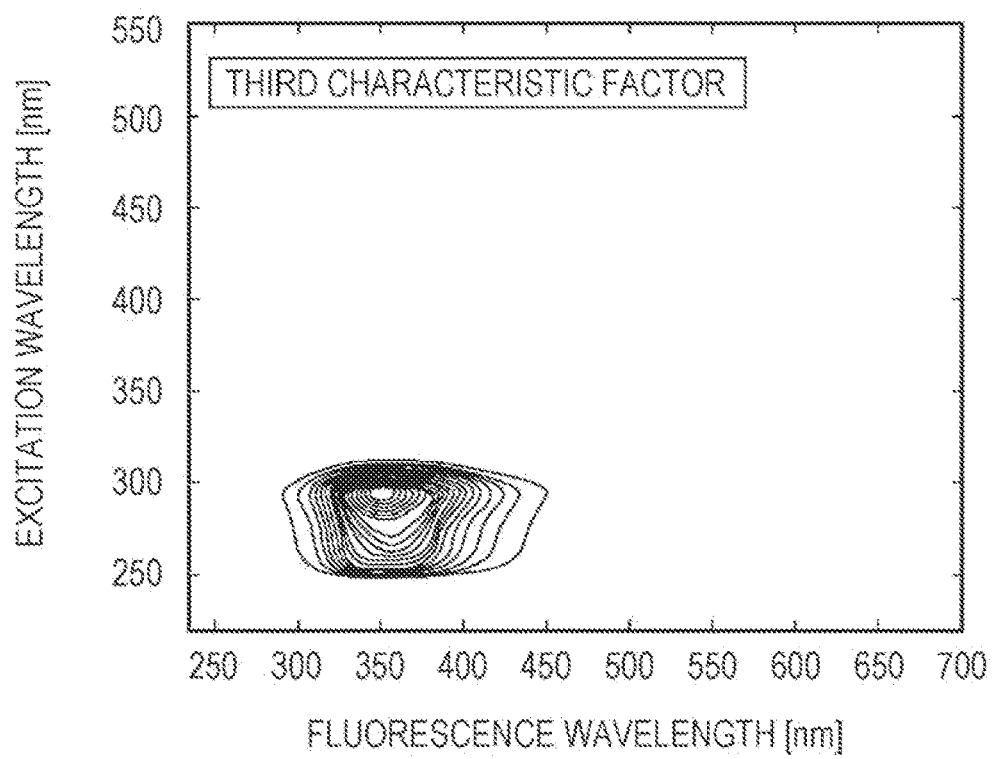
FIG. 7C illustrates three-dimensional spectral data of a third characteristic factor separated by PARAFAC.
Figure 7D:
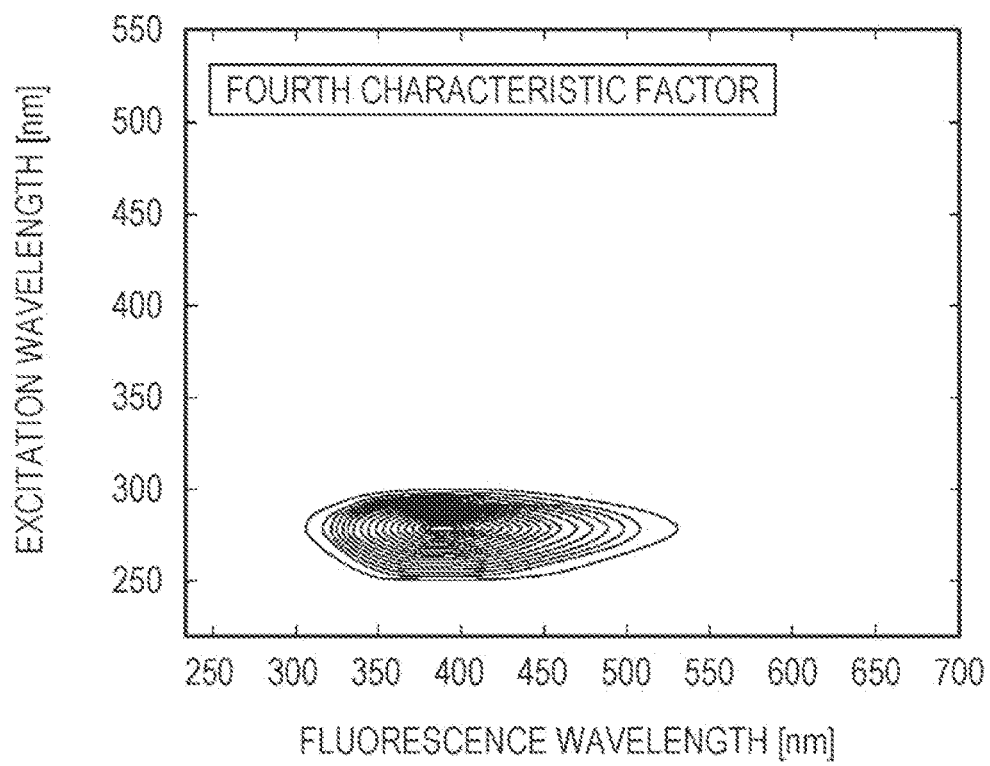
FIG. 7D illustrates three-dimensional spectral data of a fourth characteristic factor separated by PARAFAC.
Figure 7E:
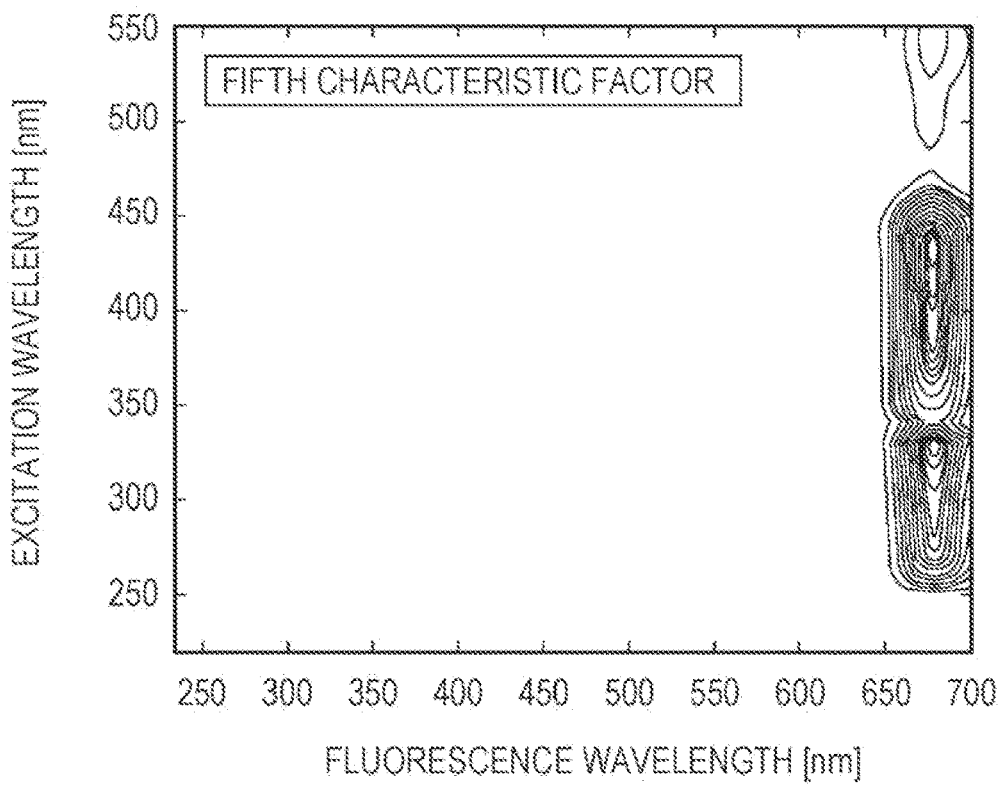
FIG. 7E illustrates three-dimensional spectral data of a fifth characteristic factor separated by PARAFAC.
Figure 7F:
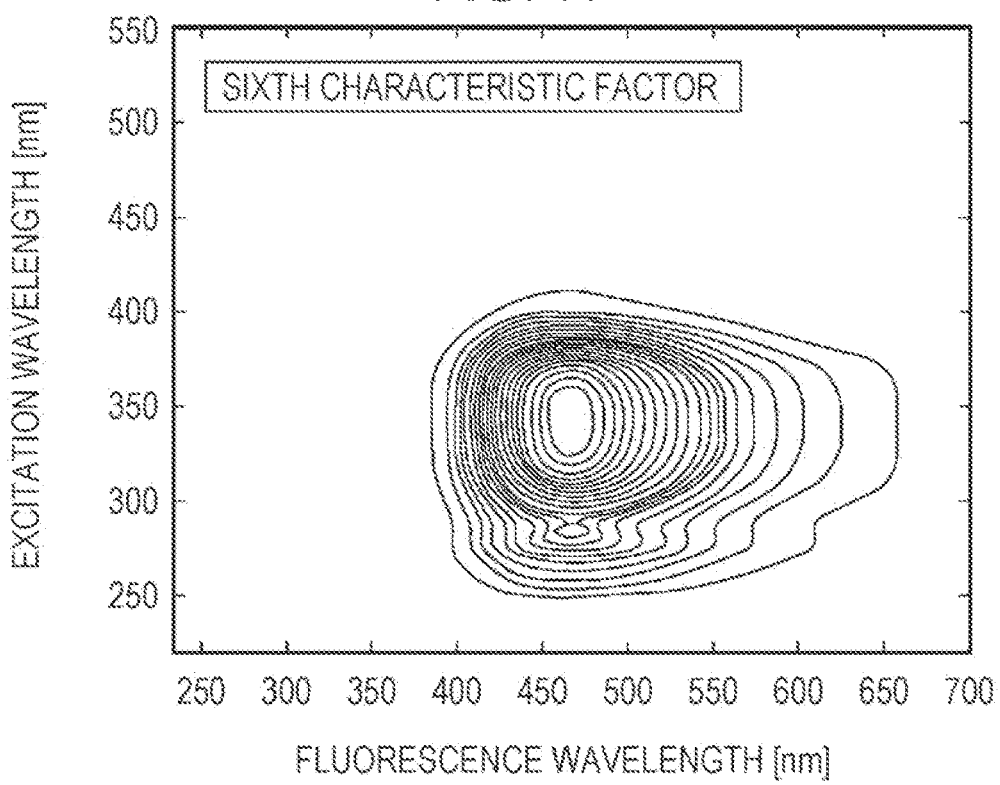
FIG. 7F illustrates three-dimensional spectral data of a sixth characteristic factor separated by PARAFAC.

For example, when the score of the second characteristic factor corresponding to tyrosine is calculated with respect to the spectral data of tyrosine illustrated in FIG. 7B, the calculated score is 100. In this case, when the score of the second characteristic factor corresponding to tyrosine is calculated with respect to the spectral data of corn, the calculated score is 5.95 as illustrated in FIG. 8. The score represents the likelihood that the characteristic factor is included in the spectral data. As the score has a lower value, it is estimated that the corresponding characteristic factor is more likely to be not included. As the score has a higher value, it is estimated that the corresponding characteristic factor is more likely to be included. The score of each characteristic factor for corn does not represent the content or the proportion of the characteristic factor in corn.

In this embodiment, as described above, the analysis unit 30 compares the score with the threshold and determines that the characteristic factor of which score exceeds the threshold is contained in the analyte 12. Assuming the threshold to be 0, in the case illustrated in FIG. 8, the analysis unit 30 identifies tyrosine, tryptophan, ATP, chlorophyll, NADH, and vitamin B2 as the components that are contained in corn. Furthermore, the analysis unit 30 identifies phenylalanine as the component that is not contained in corn.

With the component analysis device 10 according to this embodiment, as described above, the component analysis can be simply executed with high accuracy by using the reference spectral data set 52.

The case of executing PARAFAC without using the reference spectral data set 52 is now described as Comparative Example.

Figure 9A:
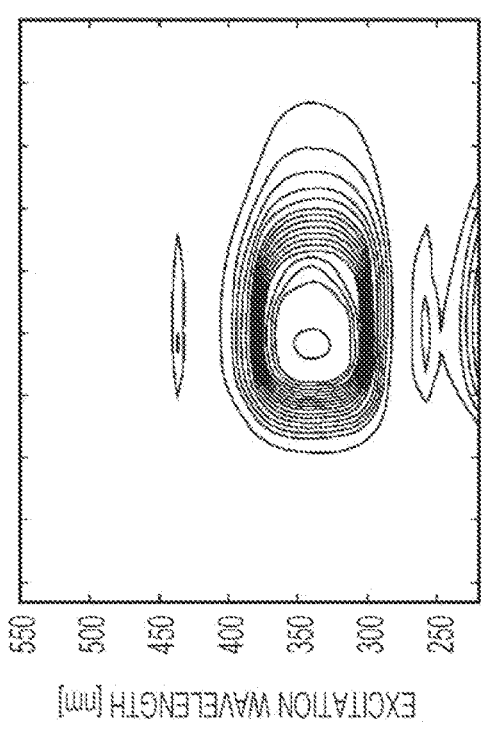
FIGS. 9A, 9B, 9C and 9D illustrate analysis results obtained by PARAFAC according to Comparative Example.
Figure 9B:
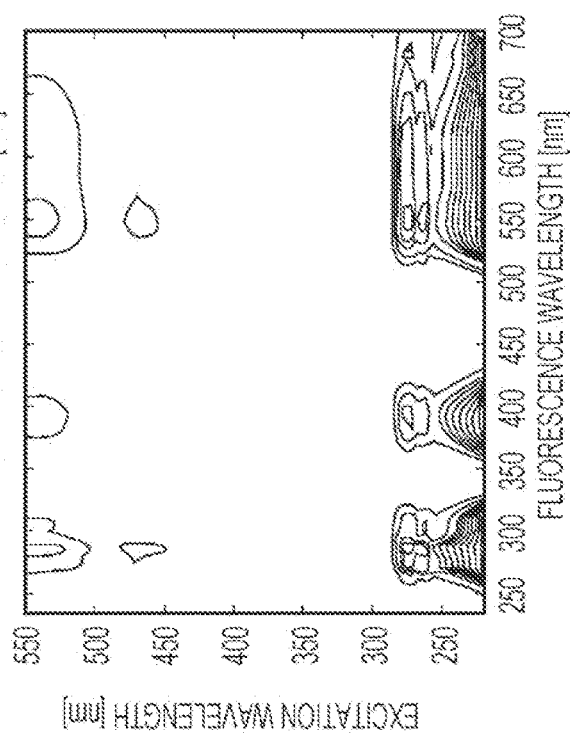
Figure 9C:
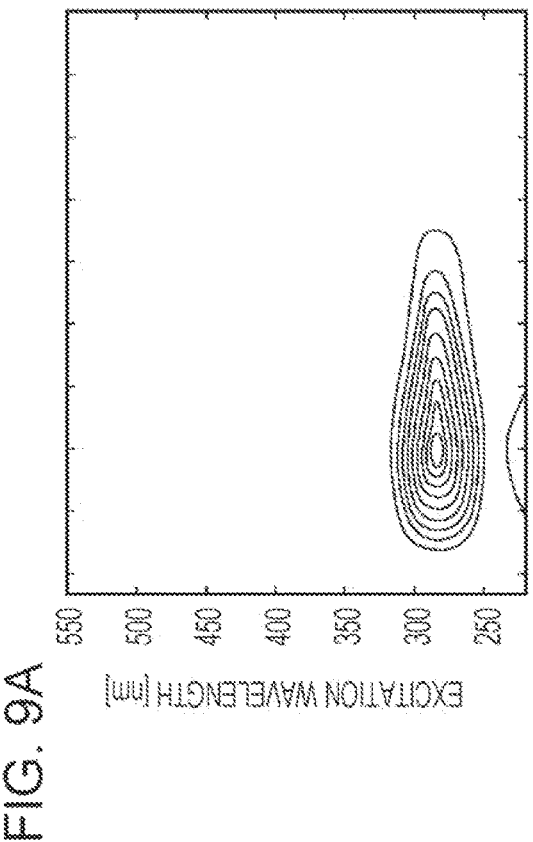
Figure 9D:
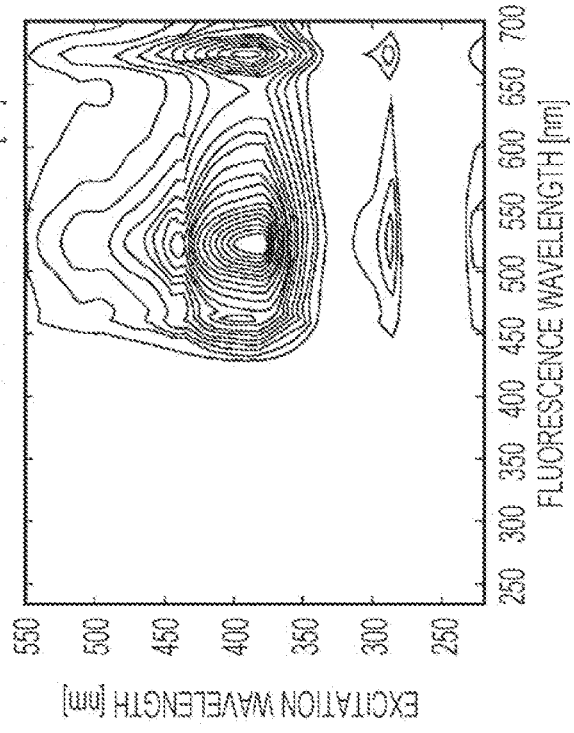

More specifically, PARAFAC was executed by using, as the input data, five EEM data based on five measurements, the measurements being each performed in a similar manner to that for the spectral data illustrated in FIG. 2. In this case, as illustrated in FIGS. 9A to 9D, separation to only four characteristic factors succeeded. Furthermore, as illustrated in FIG. 9D, a result usually not produced from the EEM data was obtained for the fourth characteristic factor. Thus, in Comparative Example, the appropriate separation result was not obtained despite increasing the number of measurements.

Other Embodiments

The component analysis device and the component analysis method according to one or more aspects have been described in connection with the embodiments, but the present disclosure is not limited to those embodiments. Modifications obtained by variously modifying the embodiments based on ideas conceivable by those skilled in the art and modifications constituted by combining constituent elements of the different embodiments also fall within the scope of the present disclosure insofar as those modifications do not depart from the gist of the present disclosure.

While the above embodiment has been described, by way of example, in connection with the case in which the factor analysis is the parallel factor analysis, the present disclosure is not limited to that case. In another case, the factor analysis may be a 3-phase factor analysis using, for example, Tucker, Tucker 2, and PARAFAC2.

While the above embodiment has been described, by way of example, in connection with the case in which the spectral data is the three-dimensional fluorescence spectral data, the present disclosure is not limited to that case. In another case, the spectral data may be spectral data that is used in a two-dimensional liquid chromatograph. Instead, the spectral data may be spectral data with a time base, namely spectral data changing over time. For example, when the component analysis is performed on multiple EEM data obtained by performing measurement at multiple different times, time-dependent changes of a component contained in the analyte can be determined. For example, it is possible to determine changes of a component, which are caused due to a chemical reaction upon application of a pharmaceutical to the analyte.

While the above embodiment has been described, by way of example, in connection with the case in which the multiple substances are substances emitting autofluorescence, the present disclosure is not limited to that case. In another case, the multiple substances may be each a substance containing a fluorescence dye, such as fluorescein, that has been artificially added.

While the above embodiment has been described, by way of example, in connection with the case in which the reference spectral data set is stored in correspondence to each type of the analyte 12, the present disclosure is not limited to that case. In another case, only the reference spectral data set corresponding to food may be stored in the storage 50, and the component analysis device 10 may be a device dedicated for identifying components contained in food.

For example, when the component analysis device 10 is the device dedicated for identifying components contained in food, there is no necessity of receiving designation of the type of the analyte 12 from the user because the type is determined in advance. Accordingly, the component analysis device 10 may not need to include the type acquisition unit 40.

In another example, the component analysis device 10 may not need to include the storage 50 for storing the reference spectral data set. The reference spectral data set may be stored in, for example, a memory in a device other than the component analysis device 10, such as an external server device. The component analysis device 10 may obtain the reference spectral data set through communication with the external server device, and may execute the factor analysis by using the obtained reference spectral data set.

While the above embodiment has been described, by way of example, in connection with the case in which the spectral light receiving unit 24 receives the fluorescence emitted from the analyte 12, the present disclosure is not limited to that case. The spectral light receiving unit 24 may receive reflected light or scattered light that is returned from the analyte 12.

Moreover, a communication method between the devices described in the above embodiment is not limited to a particular one. When wireless communication is performed between the devices, a wireless communication method (communication standards) is implemented as near field communication using, for example, ZigBee (registered trademark), Bluetooth (registered trademark), wireless LAN (Local Area Network), or the like. Alternatively, the wireless communication method (communication standards) may be implemented as communication via a wide area communication network such as the Internet. Alternatively, wired communication may be performed between the devices instead of the wireless communication. More specifically, the wired communication is, for example, PLC (Power Line Communication) or communication using wired LAN.

In the above embodiment, the processing to be executed by a particular processing unit may be executed by another processing unit. Furthermore, the sequence of multiple processing procedures may be changed, or the multiple processing procedures may be executed in parallel. In addition, distribution of the constituent elements in the component analysis device to other multiple devices is merely one example. In an example, some of the constituent elements in one device may be included in one or more other devices.

The processing procedures described in the above embodiment may be implemented with concentrated processing using a single device (system) or with distributed processing using multiple devices. One or more processors may be used to execute the programs. In other words, the concentrated processing or the distributed processing may be optionally used to execute the processing procedures.

In the above embodiment, all or part of the constituent elements, such as the control unit, may be constituted by dedicated hardware or may be realized with execution of a software program suitable for each of the constituent elements. The constituent elements may be each realized with a program execution unit, such as a CPU (Central Processing Unit) or a processor, reading and executing the software program recorded on a recording medium such as a HDD (Hard Disk Drive) or a semiconductor memory.

The constituent elements, such as the control unit, may be constituted by one or more electronic circuits. One or more electronic circuits may be each a universal circuit or a dedicated circuit.

The one or more electronic circuits may include a semiconductor device, an IC (Integrated Circuit), a LSI (Large Scale Integration), or the like. The IC or the LSI may be integrated on one chip or multiple chips. Although the term "IC" or "LSI" is used here, the name of that type of semiconductor device is changed depending on a degree of integration, and it may also be called a system LSI, a VLSI (Very Large Scale Integration), or a ULSI (Ultra Large Scale Integration). In addition, a FPGA (Field Programmable Gate Array) that is programmable after manufacturing of the LSI may also be used for the same purpose.

The generic or specific aspects of the present disclosure may be each realized with a system, a device, a method, an integrated circuit, or a computer program. In another case, those generic or specific aspects may be each realized with a non-transitory computer-readable recording medium, such as an optical disk, a HDD, or a semiconductor memory, in which the program system is stored. In still another case, those generic or specific aspects may be each realized with any suitable combination of a system, a device, a method, an integrated circuit, a computer program, and a recording medium.

The above embodiment may be subjected to various modifications, replacements, additions, omissions, and so on insofar as not departing from the scope of Claims or the equivalent scope thereof.

The present disclosure can be utilized as a component analysis device capable of simply performing a component analysis of an analyte with high accuracy and can be applied to, for example, a water quality inspection device, a contaminant detection device, a contaminant removable device, or the like.

What is claimed is:

1. A component analysis device comprising:
    a data acquisition circuit that acquires spectral data of an analyte containing components, the spectral data being obtained by measuring a spectrum of the analyte with a sensor;
    a type acquisition circuit that acquires information indicating a type of the analyte;
    a storage that stores a reference spectral data set including multiple spectral data of substances each of which is estimated to be included in the analyte, the reference spectral data set corresponding to the type of the analyte; and
    an analysis circuit that performs a parallel factor analysis by using, as input data, the spectral data of the analyte and the reference spectral data set,
    wherein the analyte is aerosol,
    the reference spectral data set corresponding to the aerosol includes pollen, and
    whether the pollen floating in air is present or absent is determined in accordance with a result of the parallel factor analysis.

2. The component analysis device according to claim 1, wherein, when the analyte contains a substance that is not included in the reference spectral data set, the analysis circuit identifies a substance that is not estimated to be included in the analyte.

3. The component analysis device according to claim 1, wherein the spectral data is three-dimensional fluorescence spectral data.

4. The component analysis device according to claim 1, wherein
the number of the spectral data of the analyte is M,
the number of the multiple spectral data included in the reference spectral data set is N, and
the analysis circuit performs the parallel factor analysis on (M+N) pieces of spectral data.

5. A component analysis method comprising:
acquiring spectral data of an analyte containing components, the spectral data being obtained by measuring a spectrum of the analyte;
acquiring information indicating a type of the analyte;
obtaining a reference spectral data set including multiple spectral data of substances each of which is estimated to be included in the analyte, the reference spectral data set corresponding to the type of the analyte; and
performing a parallel factor analysis by using, as input data, the spectral data of the analyte and the reference spectral data set,
wherein the analyte is aerosol,
the reference spectral data set corresponding to the aerosol includes pollen, and
whether the pollen floating in air is present or absent is determined in accordance with a result of the parallel factor analysis.

6. A non-transitory computer-readable recording medium storing a program to execute a component analysis of an analyte,
wherein, when the program is executed by a computer, the computer executes:
acquiring spectral data of an analyte containing components, the spectral data being obtained by measuring a spectrum of the analyte;
acquiring information indicating a type of the analyte;
obtaining a reference spectral data set including multiple spectral data of substances each of which is estimated to be included in the analyte, the reference spectral data set corresponding to the type of the analyte; and
performing a parallel factor analysis by using, as input data, the spectral data of the analyte and the reference spectral data set,
wherein the analyte is aerosol,
the reference spectral data set corresponding to the aerosol includes pollen, and
whether the pollen floating in air is present or absent is determined in accordance with a result of the parallel factor analysis.

\* \* \* \* \*